United States Patent
Maghribi et al.

(10) Patent No.: US 7,265,298 B2
(45) Date of Patent: *Sep. 4, 2007

(54) SERPENTINE AND CORDUROY CIRCUITS TO ENHANCE THE STRETCHABILITY OF A STRETCHABLE ELECTRONIC DEVICE

(75) Inventors: Mariam N. Maghribi, Livermore, CA (US); Peter A. Krulevitch, Pleasanton, CA (US); Thomas S. Wilson, Castro Valley, CA (US); Julie K. Hamilton, Tracy, CA (US); Christina Park, Cambridge, MA (US)

(73) Assignee: The Regents of the University of California, Oakland, CA (US)

( * ) Notice: Subject to any disclaimer, the term of this patent is extended or adjusted under 35 U.S.C. 154(b) by 464 days.

This patent is subject to a terminal disclaimer.

(21) Appl. No.: 10/826,477

(22) Filed: Apr. 16, 2004

(65) Prior Publication Data
US 2004/0238819 A1 Dec. 2, 2004

Related U.S. Application Data

(60) Provisional application No. 60/474,862, filed on May 30, 2003.

(51) Int. Cl.
*H05K 1/00* (2006.01)
(52) U.S. Cl. .............. 174/254; 174/258; 428/209; 428/447; 428/465
(58) Field of Classification Search .............. 428/167, 428/169, 209, 447, 465; 174/254, 258
See application file for complete search history.

(56) References Cited

U.S. PATENT DOCUMENTS

| 3,168,617 | A | * | 2/1965 | Richter ................ 174/117 FF |
| 5,346,850 | A | | 9/1994 | Kaschmitter et al. |
| 5,363,114 | A | * | 11/1994 | Shoemaker ................ 343/828 |
| 5,395,481 | A | | 3/1995 | McCarthy |
| 5,414,276 | A | | 5/1995 | McCarthy |
| 5,496,970 | A | * | 3/1996 | Spencer ................ 174/117 F |
| 5,612,999 | A | | 3/1997 | Gardenhour, Jr. et al. |
| 5,625,169 | A | * | 4/1997 | Tanaka ................ 174/250 |
| 5,681,662 | A | * | 10/1997 | Chen et al. ................ 428/607 |
| 5,817,550 | A | | 10/1998 | Carey et al. |
| 6,324,429 | B1 | | 11/2001 | Shire et al. |

(Continued)

FOREIGN PATENT DOCUMENTS

EP    0 536 636 A1    4/1993

(Continued)

*Primary Examiner*—Cathy F. Lam
(74) *Attorney, Agent, or Firm*—Eddie E. Scott; John H. Lee

(57) ABSTRACT

A stretchable electronic apparatus and method of producing the apparatus. The apparatus has a central longitudinal axis and the apparatus is stretchable in a longitudinal direction generally aligned with the central longitudinal axis. The apparatus comprises a stretchable polymer body, and at least one circuit line operatively connected to the stretchable polymer body, the at least one circuit line extending in the longitudinal direction and having a longitudinal component that extends in the longitudinal direction and having an offset component that is at an angle to the longitudinal direction, the longitudinal component and the offset component allowing the apparatus to stretch in the longitudinal direction while maintaining the integrity of the at least one circuit line.

14 Claims, 2 Drawing Sheets

U.S. PATENT DOCUMENTS

| | | |
|---|---|---|
| 7,005,179 B2 * | 2/2006 | Davidson et al. ........... 428/209 |
| 7,035,692 B1 * | 4/2006 | Maghribi et al. ............. 607/53 |
| 7,036,220 B2 * | 5/2006 | Davidson et al. ............. 29/846 |
| 2001/0016683 A1 | 8/2001 | Darrow et al. |
| 2003/0097165 A1 | 5/2003 | Krulevitch et al. |
| 2003/0097166 A1 | 5/2003 | Krulevitch et al. |

FOREIGN PATENT DOCUMENTS

| | | |
|---|---|---|
| EP | 101 03 503 A1 | 8/2002 |
| GB | J18326 A | 0/1909 |

* cited by examiner

US 7,265,298 B2

SERPENTINE AND CORDUROY CIRCUITS TO ENHANCE THE STRETCHABILITY OF A STRETCHABLE ELECTRONIC DEVICE

CROSS-REFERENCE TO RELATED APPLICATIONS

This application claims the benefit of U.S. Provisional Patent Application No. 60/474,862 filed May 30, 2003 and titled "Serpentine and corduroy designs to enhance the stretchablity of metalized silicone." U.S. Provisional Patent Application No. 60/474,862 filed May 30, 2003 and titled "Serpentine and corduroy designs to enhance the stretchablity of metalized silicone" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to electronic devices and more particularly to a stretchable electronic device.

2. State of Technology

U.S. Pat. No. 5,817,550 for a method for formation of thin film transistors on plastic substrates to Paul G. Carey, Patrick M. Smith, Thomas W. Sigmon, and Randy C. Aceves, issued Oct. 6, 1998, provides the following state of technology information, "Recently a process was developed for crystallizing and doping amorphous silicon on a low cost, so-called low-temperature plastic substrate using a short pulsed high energy source in a selected environment, without heat propagation and build-up in the substrate so as to enable use of plastic substrates incapable of withstanding sustained processing temperatures higher than about 180° C. Such a process is described and claimed in U.S. Pat. No. 5,346,850 issued Sep. 13, 1994 to J. L. Kaschmitter et al., assigned to the Assignee of the instant application. Also, recent efforts to utilize less expensive and lower temperature substrates have been carried out wherein the devices were formed using conventional temperatures on a sacrificial substrate and then transferred to another substrate, with the sacrificial substrate thereafter removed. Such approaches are described and claimed in U.S. Pat. No. 5,395,481 issued Mar. 7, 1995, U.S. Pat. No. 5,399,231 issued Mar. 21, 1995, and U.S. PAt. No. 5,414,276 issued May 9, 1995, each issued to A. McCarthy and assigned to the assignee of the instant application."

U.S. Pat. No. 6,324,429 for a chronically implantable retinal prosthesis by Doug Shire, Joseph Rizzo, and John Wyatt, of the Massachusetts Eye and Ear Infirmary Massachusetts Institute of Technology issued Nov. 27, 2001 provides the following state of technology information, "In the human eye, the ganglion cell layer of the retina becomes a monolayer at a distance of 2.5-2.75 mm from the foveal center. Since the cells region, this is the preferred location for stimulation with an epiretinal electrode array. The feasibility of a visual prosthesis operating on such a principle has been demonstrated by Humayun, et al. in an experiment in which the retinas of patients with retinitis pigmentosa, age-related macular degeneration, or similar degenerative diseases of the eye were stimulated using bundles of insulated platinum wire."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides stretchable electronic apparatus and method of producing the apparatus. The apparatus has a central longitudinal axis and the apparatus is stretchable in a longitudinal direction generally aligned with the central longitudinal axis. The apparatus comprises a stretchable polymer body, and at least one circuit line operatively connected to the stretchable polymer body, the at least one circuit line extending in the longitudinal direction and having a longitudinal component that extends in the longitudinal direction and having an offset component that is at an angle to the longitudinal direction, the longitudinal component and the offset component allowing the apparatus to stretch in the longitudinal direction while maintaining the integrity of the at least one circuit line. In one embodiment the longitudinal component that extends in the longitudinal direction and the offset component that is at an angle to the longitudinal direction comprise a 2-D serpentine circuit producing a spring in the at least one circuit line. In another embodiment, the longitudinal component that extends in the longitudinal direction and the offset component that is at an angle to the longitudinal direction comprise a 3-D corduroy circuit producing stress relieves structures in the at least one circuit line.

The apparatus has many uses. This includes use in shaped acoustic sensors and transmitters; biological, chemical, temperature, and radiation sensors; sensors and stimulators for interfacing with human body and inanimate objects; non-destructive evaluation sensors; flexible display monitors; smart notes; and monitoring devices. The apparatus also has uses in implantable devices including epiretinal, subretinal, and cortical artificial vision implants, cochlear implants, neurological implants, spinal cord implants and other neural interface implants; implantable and transdermal drug delivery devices; monitoring devices; implantable ribbon cables and electrode array for deep brain stimulation, spinal cord reattachment, nerve regeneration, cortical implants, retinal implants, cochlear implants, drug delivery, muscle stimulation and relaxation; and flexible displays and smart notes, conformable circuits as well as other uses.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
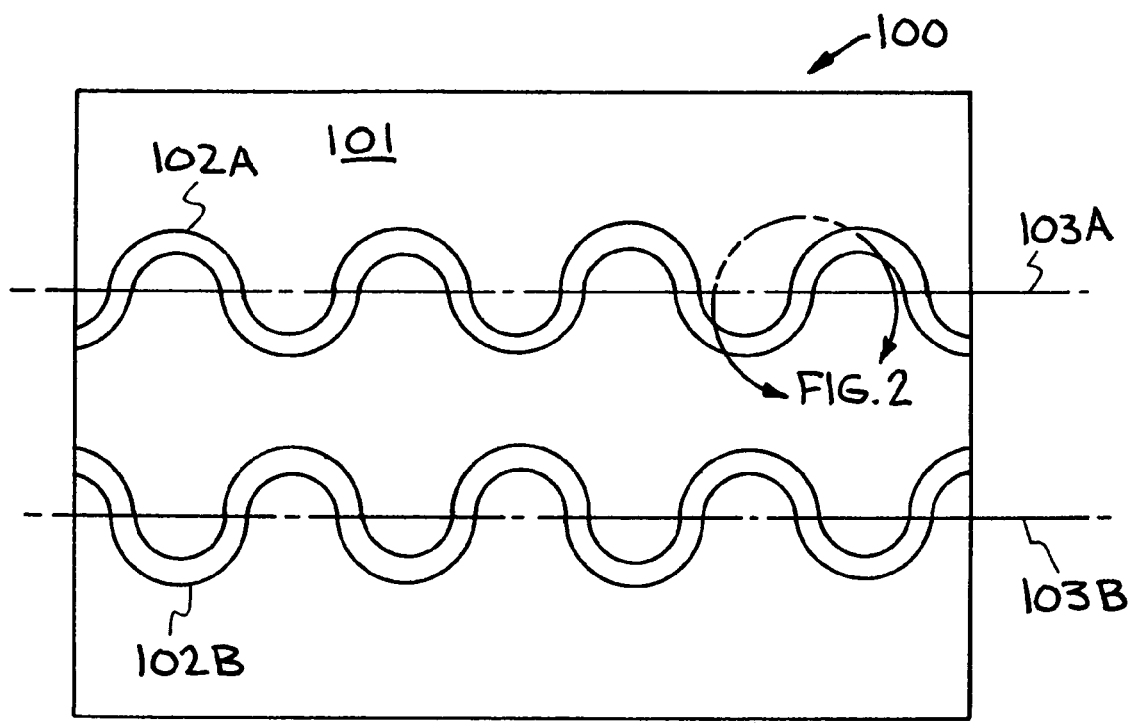
FIG. 1 illustrates an embodiment of a circuit constructed in accordance with the present invention.

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to in FIG. 1, an embodiment of an apparatus constructed in accordance with the present invention is illustrated. The apparatus is generally designated by the reference numeral 100. The embodiment 100 provides a stretchable electronic circuit or electronic device 100. FIG. 1 also serves to illustrate an embodiment of the invention that provides a polymer-based process to produce a circuit or electronic device containing stretchable a conducting circuit.

The apparatus 100 has uses in shaped acoustic sensors and transmitters; biological, chemical, temperature, and radiation sensors; sensors and stimulators for interfacing with human body and inanimate objects; non-destructive evaluation sensors; flexible display monitors; smart notes; and monitoring devices. The apparatus 100 also has uses in implantable devices including epiretinal, subretinal, and cortical artificial vision implants, cochlear implants, neurological implants, spinal cord implants and other neural interface implants; implantable and transdermal drug delivery devices; monitoring devices; implantable ribbon cables and electrode array for deep brain stimulation, spinal cord reattachment, nerve regeneration, cortical implants, retinal implants, cochlear implants, drug delivery, muscle stimulation and relaxation; and flexible displays and smart notes, conformable circuits as well as other uses.

The apparatus 100 comprises a stretchable electronic apparatus having a central longitudinal axis. The apparatus 100 is stretchable in a longitudinal direction generally aligned with the central longitudinal axis of the apparatus 100. The apparatus 100 utilizes a stretchable polymer body 101 and at least one circuit line operatively connected to the stretchable polymer body 101. Circuit lines 102A and 102B are shown for illustrative purposes. As illustrated by FIG. 1, circuit lines 102A and 102B extend in the longitudinal direction represented by the longitudinal axes 103A and 103B. The longitudinal axes 103A and 103B extend generally parallel to the longitudinal axis of the apparatus 100. Each circuit line 102A and 102B has a longitudinal component that extends in the longitudinal direction and has an offset component that is at an angle to the longitudinal direction. The longitudinal portion and the offset portion allow the apparatus 100 to stretch in the longitudinal direction while maintaining the integrity of the circuit lines 102A and 102B.

Figure 2:
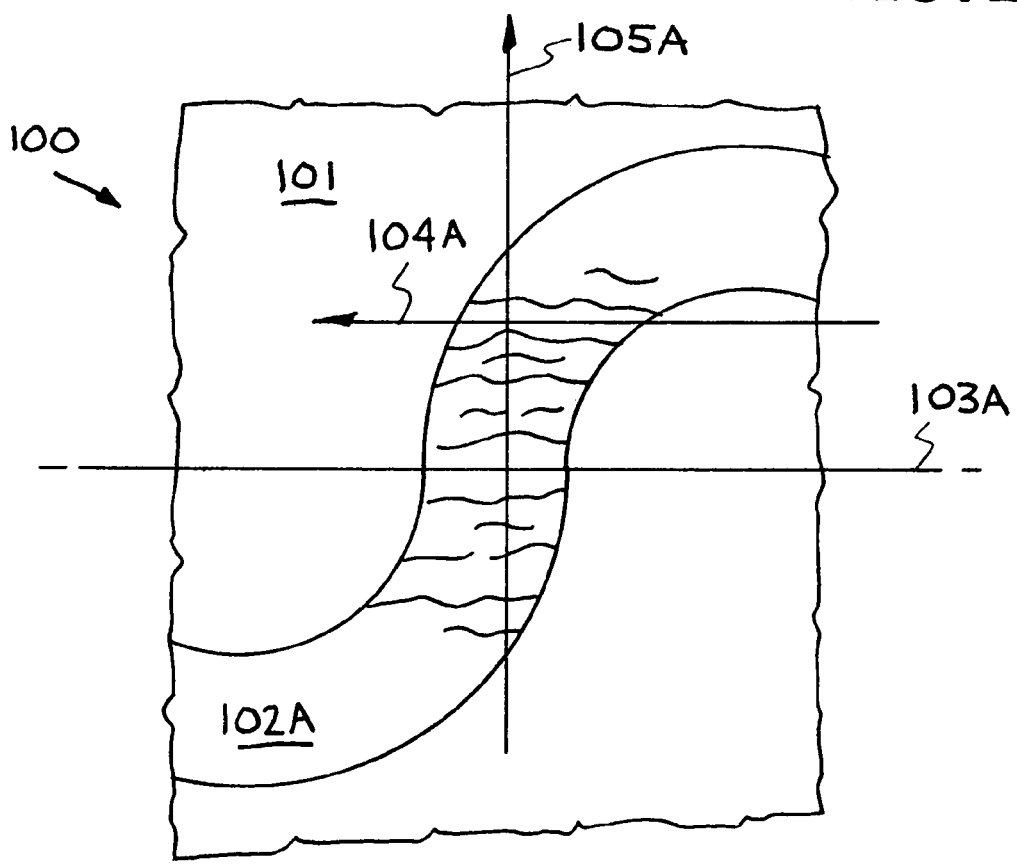
FIG. 2 is an enlarged view of a section of the circuit shown in FIG. 1.

Referring now to FIG. 2, an enlarged view of a portion of the circuit line 102A of FIG. 1 is shown. The circuit line 102A extends in a longitudinal direction represented by the longitudinal axis 103A. The longitudinal axis 103A extends generally parallel to the longitudinal axis of the apparatus 100. The circuit line 102A has a longitudinal component 104A that extends in the longitudinal direction and has an offset component 105A that is at an angle to the longitudinal direction. The longitudinal portion 104A and the offset portion 105A of the circuit line 102A allow the apparatus 100 to stretch in the longitudinal direction while maintaining the integrity of the circuit lines 102A and 102B.

The apparatus 100 uses dimethylsiloxane (PDMS) as the stretchable polymer body 101. The stretchable polymer body 101 can be made in batch processes and provides a low-cost device that is ready for implantation without the need for additional packaging steps. The metal features are patterned (deposited) on the stretchable polymer body 101. The stretchable polymer body 101 is fabricated using PDMS which is an inert biocompatible elastomeric material that has simultaneously low water and high oxygen permeability. The conformable nature of PDMS is useful for ensuring uniform contact with the curved surfaces. PDMS is a form of silicone rubber, a material that is used in many implants and has been demonstrated to withstand the body's chemical and physical conditions without causing adverse side effects, suggesting that PDMS may be a favorable material to implant within the body. Robustness of the metalized PDMS is another important design criterion because as stretching and bending occur during fabrication and implantation of the device 100.

The processes that can be used to produce the polydimethylsiloxane (PDMS) stretchable polymer body 101 are described in greater detail in U.S. patent applications Ser. Nos. 2003/0097165 and 2003/0097166 and in the dissertation titled, "MICROFABRICATION OF AN IMPLANTABLE SILICONE MICROELECTRODE ARRAY FOR AN EPIRETINAL PROSTHESIS," submitted in partial satisfaction of the requirements for the degree of Doctor of Philosophy in Biomedical Engineering by one of the inventors Mariam N. Maghribi, University of California, Davis June 2003. The dissertation formed part of U.S. Provisional Patent Application No. 60/474,862 filed May 30, 2003 and priority of U.S. Provisional Patent Application No. 60/474, 862 filed May 30, 2003 is claimed in this application. The disclosures of U.S. patent applications Ser. Nos. 2003/0097165 and 2003/0097166 and the dissertation are incorporated herein by reference.

Figure 3:
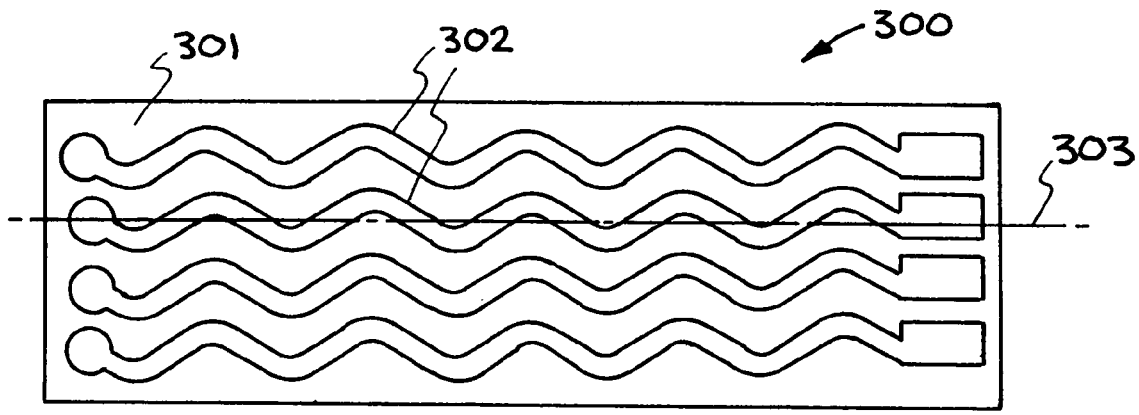
FIG. 3 is a top view of another embodiment of a circuit constructed in accordance with the present invention.

Referring now to FIG. 3 another embodiment of an apparatus constructed in accordance with the present invention is illustrated. The apparatus is generally designated by the reference numeral 300. The apparatus 300 provides a serpentine stretchable electronic circuit 302 in an electronic device 300. FIG. 3 also serves to illustrate an embodiment of the invention that provides a polymer-based process to produce an electronic device 300 containing serpentine stretchable conducting circuits illustrated by circuit 302. The process described above in connection with apparatus 100 can be used to produce the apparatus 300.

The apparatus 300 has many uses including the uses identified above for the apparatus 100. One important use for the apparatus 300 is in implantable biomedical microdevice electrode and interconnect formation. Other uses include biocompatible interconnects for a multitude of surgical implants; implantable, biocompatible electrical interconnect cabling; polymer based microelectrodes; polymer-based multilevel and multicomponent systems interconnect; applications requiring flexible and stretchable electrical interconnect; fanout metalization for connectorization of integrated PDMS Microsystems; compact, hermetically sealed, high conductor density cabling; flexible and stretchable electrically conducting interconnect for compact consumer electronic products, internal and external medical device interconnect; implantable devices; epiretinal, subretinal, and cortical artificial vision implant, cochlear implants, neurological implants, spinal cord implants and other neural interface implants; implantable and transdermal drug delivery devices; monitoring devices; implantable ribbon cables and electrode array for deep brain stimulation, spinal cord reattachment, nerve regeneration, cortical implants, retinal implants, cochlear implants, drug delivery, muscle stimulation and relaxation; flexible displays and smart notes, conformable circuits; low weight and profile high density conductors for aviation; and insulated interconnect cabling for aquatic applications such as environmental monitoring.

The serpentine circuits in the electronic apparatus 300 have central longitudinal axes illustrated by longitudinal axis 303 of circuit 302. The apparatus 300 is stretchable in a longitudinal direction generally aligned with the central longitudinal axis of the apparatus 300. The apparatus 300 comprises a stretchable polymer body 301 and the circuit lines operatively connected to the stretchable polymer body 301. As illustrated by FIG. 3, the circuit lines extend in the longitudinal direction as illustrated represented by the longitudinal axis 303 of circuit 302. Each circuit line has a longitudinal component that extends in the longitudinal direction and has an offset component that is at an angle to the longitudinal direction. The longitudinal portion and the offset portion allow the apparatus 300 to stretch in the longitudinal direction while maintaining the integrity of the circuit lines.

The view of the apparatus 300 shown in FIG. 3 is a top view. The serpentine circuit 302 is a 2-D embodiment of a circuit incorporating a spring-like pattern to relieve the stress in the thin film therefore enhancing the stretchablity by increasing the percent strain of the metal traces 302 on the PDMS substrate body 301. The apparatus 300 can be fabricated using traditional photolithographic patterning techniques. The serpentine circuit 302 has a longitudinal component that extends in the longitudinal direction and has an offset component that is at an angle to the longitudinal direction. The longitudinal component that extends in the longitudinal direction and the offset component that is at an angle to the longitudinal direction extend laterally from the longitudinal axis 303 of the serpentine circuit 302.

Figure 4:
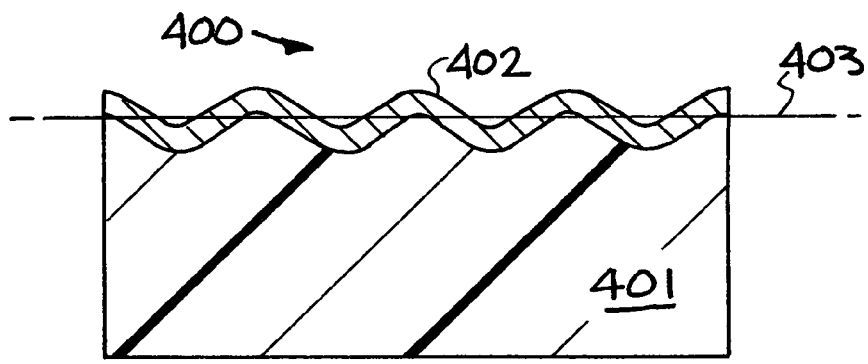
FIG. 4 is yet another embodiment of a circuit constructed in accordance with the present invention.
Figure 5:
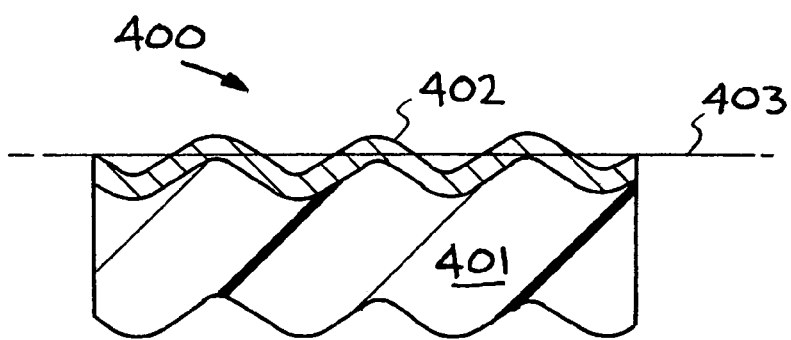
FIG. 5 is a top view of the circuit shown in FIG. 4.

Referring now to FIGS. 4 and 5, yet another embodiment of an apparatus constructed in accordance with the present invention is illustrated. The apparatus is generally designated by the reference numeral 400. The embodiment 400 provides a corduroy stretchable electronic circuit 402 in an electronic device 400. FIGS. 4 and 5 also serve to illustrate an embodiment of the invention that provides a polymer-based process to produce an electronic device 400 containing a corduroy stretchable conducting circuit 402. The process described above in connection with apparatus 100 can be used to produce the apparatus 400.

The apparatus 400 has uses in shaped acoustic sensors and transmitters; biological, chemical, temperature, and radiation sensors; sensors and stimulators for interfacing with human body and inanimate objects; non-destructive evaluation sensors; flexible display monitors; smart notes; and monitoring devices. The apparatus 100 also has uses in implantable devices including epiretinal, subretinal, and cortical artificial vision implants, cochlear implants, neurological implants, spinal cord implants and other neural interface implants; implantable and transdermal drug delivery devices; monitoring devices; implantable ribbon cables and electrode array for deep brain stimulation, spinal cord reattachment, nerve regeneration, cortical implants, retinal implants, cochlear implants, drug delivery, muscle stimulation and relaxation; and flexible displays and smart notes, conformable circuits as well as other uses.

Referring now to FIG. 4, the apparatus 400 includes a corduroy circuit 402 with a central longitudinal axis 403. The central longitudinal axis 403 of the corduroy circuit 402 is generally parallel to the central longitudinal axis to the apparatus 400. The apparatus 400 is stretchable in a longitudinal direction generally aligned with the central longitudinal axis of the apparatus 400 and the central longitudinal axis 403 of the corduroy circuit 402. The process described above in connection with apparatus 100 can be used to produce the apparatus 400.

Referring now to FIG. 5, a cross-sectional view of the apparatus 400 is show. The apparatus 400 comprises a stretchable polymer body 401 and a circuit line 402 operatively connected to the stretchable polymer body 401. The circuit line 402 extends in the longitudinal direction and as illustrated by FIG. 5 the circuit line 402 extends in a vertical direction above and below the longitudinal axis 403. The circuit line 402 therefore has a longitudinal component that extends in a longitudinal direction and has an axial component that is at an angle to the longitudinal direction. The longitudinal portion and the offset portion allow the apparatus 400 to stretch in the longitudinal direction while maintaining the integrity of the circuit line 402. The serpentine circuit 402 is a 3-D embodiment incorporating stress relieves structures. In addition to photolithography, molding was required to achieve the 3-D rippled structure in the PDMS.

The apparatus 400 uses dimethylsiloxane (PDMS) as the stretchable polymer body 401. The stretchable polymer body 401 can be made in batch processes and provides a low-cost device that is ready for implantation without the need for additional packaging steps. The metal features are patterned (deposited) on the stretchable polymer body 401. The stretchable polymer body 401 is fabricated using PDMS which is an inert biocompatible elastomeric material that has simultaneously low water and high oxygen permeability. The conformable nature of PDMS is useful for ensuring uniform contact with the curved surfaces. PDMS is a form of silicone rubber, a material that is used in many implants and has been demonstrated to withstand the body's chemical and physical conditions without causing adverse side effects, suggesting that PDMS may be a favorable material to implant within the body. Robustness of the metalized PDMS is another important design criterion because as stretching and bending occur during fabrication and implantation of the device 400.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A stretchable electronic apparatus, the apparatus having a central longitudinal axis and the apparatus being stretchable in a longitudinal direction generally aligned with the central longitudinal axis, comprising:
    a stretchable polymer body, and
    at least one circuit line operatively connected to said stretchable polymer body, said at least one circuit line extending in the longitudinal direction and having
    a multiplicity of stretching portions, each of said stretching portions having
    a longitudinal component that extends in the longitudinal direction and having
    an offset component that is at an angle to the longitudinal direction,
    said longitudinal component and said offset component allowing said stretching portions to stretch in the longitudinal direction while maintaining the integrity of said at least one circuit line.

2. The stretchable electronic apparatus of claim 1 wherein said longitudinal component that extends in the longitudinal direction and said offset component that is at an angle to the longitudinal direction comprise a 2-D serpentine circuit producing a spring in said at least one circuit line.

3. The stretchable electronic apparatus of claim 1 wherein said at least one circuit line has a circuit line longitudinal axis that extends generally parallel to the central longitudinal axis of the electronic apparatus and wherein said longitudinal component that extends in the longitudinal direction and said offset component that is at an angle to the longitudinal direction extend laterally from said circuit line longitudinal axis.

4. The stretchable electronic apparatus of claim 1 wherein said longitudinal component that extends in the longitudinal direction and said offset component that is at an angle to the longitudinal direction comprise a 3-D corduroy circuit producing stress relieves structures in said at least one circuit line.

5. The stretchable electronic apparatus of claim 1 wherein said at least one circuit line has a circuit line longitudinal axis that extends generally parallel to the central longitudinal axis of the electronic apparatus and wherein said longitudinal component that extends in the longitudinal direction and said offset component that is at an angle to the longitudinal direction extend in a vertical direction above and below said circuit line longitudinal axis.

6. The stretchable electronic apparatus of claim 1 wherein said stretchable polymer body is silicone.

7. The stretchable electronic apparatus of claim 1 wherein said stretchable polymer body comprises poly(dimethylsiloxane).

8. The stretchable electronic apparatus of claim 1 wherein said at least one circuit line comprises a conductive micronscale wire.

9. The stretchable electronic apparatus of claim 1 wherein said at least one circuit line comprises a conductive metal paste.

10. The stretchable electronic apparatus of claim 1 wherein said at least one circuit line comprises a photolytic metal material.

11. The stretchable electronic apparatus of claim 1 wherein said at least one circuit line comprises a conductive polymer.

12. The stretchable electronic apparatus of claim 1 wherein said stretchable polymer body comprises a microcable.

13. The stretchable electronic apparatus of claim 1 wherein said at least one circuit line has a circuit line longitudinal axis that extends generally parallel to the central longitudinal axis of the electronic apparatus and wherein said longitudinal component that extends in the longitudinal direction and said offset component that is at an angle to the longitudinal direction extend both laterally from said circuit line longitudinal axis and vertically above and below said circuit line longitudinal axis.

14. The stretchable electronic apparatus of claim 1 wherein said at least one circuit line has a circuit line longitudinal axis that extends generally parallel to the central longitudinal axis of the electronic apparatus, said circuit line having a first section with a longitudinal component that extends in the longitudinal direction and an offset component that is at an angle to the longitudinal direction and extends laterally from said circuit line longitudinal axis, and a second section with a longitudinal component that extends in the longitudinal direction and an offset component that is at an angle to the longitudinal direction and extends vertically above and below said circuit line longitudinal axis.

* * * * *